United States Patent [19]

Van Os

[11] Patent Number: 5,658,595

[45] Date of Patent: Aug. 19, 1997

[54] METHOD, COMPOSITION AND DEVICE FOR THE TREATMENT OF RAW MATERIALS, PRODUCTS AND PRODUCTION MEANS, IN PARTICULAR IN THE FOODSTUFFS INDUSTRY

[75] Inventor: Jan Van Os, Hoedenkenskerke, Netherlands

[73] Assignee: Kon-Des Milieutechnologie B.V., Amsterdam, Netherlands

[21] Appl. No.: 204,330

[22] PCT Filed: Sep. 10, 1992

[86] PCT No.: PCT/NL92/00156

§ 371 Date: May 10, 1994

§ 102(e) Date: May 10, 1994

[87] PCT Pub. No.: WO93/04595

PCT Pub. Date: Mar. 18, 1993

[30] Foreign Application Priority Data

Sep. 10, 1991 [NO] Norway .................................. 913559
Jul. 2, 1992 [NL] Netherlands ........................... 9201178

[51] Int. Cl.⁶ ......................... A01N 59/00; A01N 31/02; A01N 37/00; A01N 37/02
[52] U.S. Cl. ............... 424/616; 514/738; 514/553; 514/557; 514/558; 514/560; 514/574; 422/28; 422/29; 422/32
[58] Field of Search .................. 424/616; 514/557, 514/738, 553, 558, 560, 574; 422/28, 32, 29; 426/532, 652

[56] References Cited

U.S. PATENT DOCUMENTS

| | | | |
|---|---|---|---|
| 4,431,631 | 2/1984 | Clipper et al. | 424/53 |
| 4,696,757 | 9/1987 | Blank et al. | 252/186.29 |
| 5,008,079 | 4/1991 | Wutzler et al. | 422/28 |
| 5,059,417 | 10/1991 | Williams et al. | 424/53 |
| 5,130,124 | 7/1992 | Merianos et al. | 424/53 |

FOREIGN PATENT DOCUMENTS

| | | |
|---|---|---|
| 0460962 | 12/1991 | European Pat. Off. . |
| 3806953 | 9/1989 | Germany . |
| 2100750 | 1/1983 | United Kingdom . |
| WO93/04705 | 3/1993 | WIPO . |

*Primary Examiner*—John Pak
*Attorney, Agent, or Firm*—Young & Thompson

[57] ABSTRACT

A mixture of hydrogen peroxide and glycerol has been found to be a particularly effective composition as a preserving additive for raw materials, in particular foodstuffs. An organic acid, such as valeric acid, can be added to the mixture as stabiliser. By atomising the mixture, in combination with gentle shaking of the product to be treated in a device provided with means suitable for this purpose, an efficient treatment is effected with relatively low consumption of the preserving mixture. The shelf life of the products treated can be further increased by drying the surface thereof using sterile air.

14 Claims, 3 Drawing Sheets

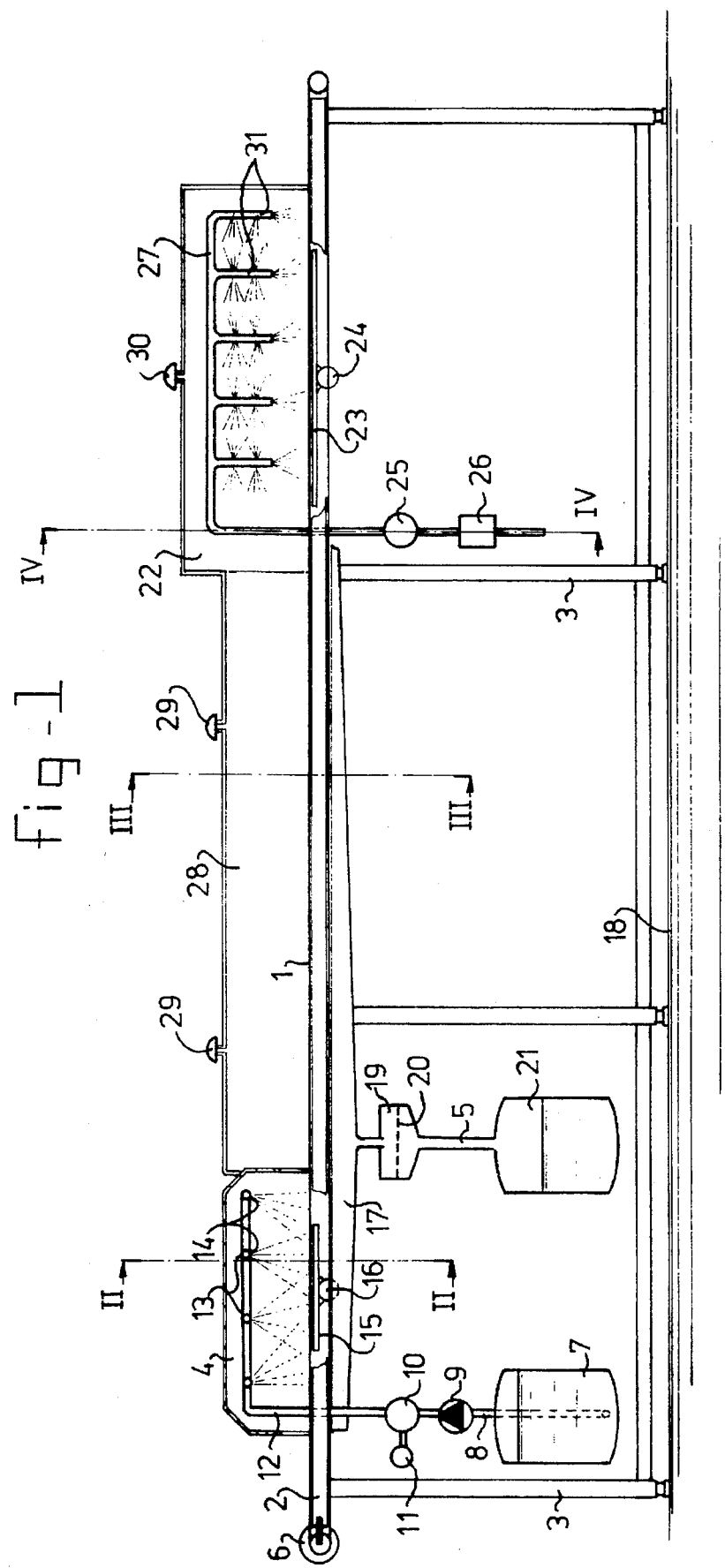

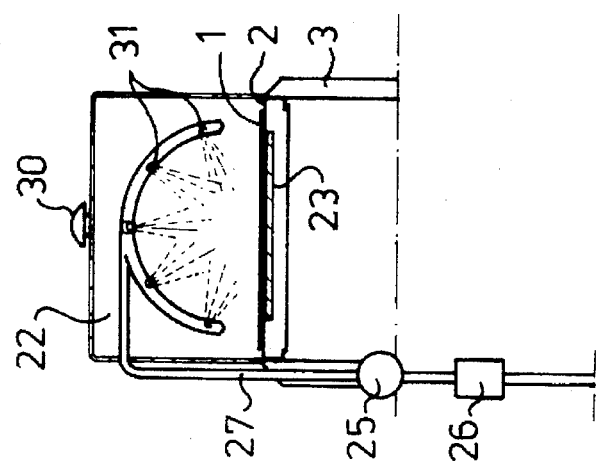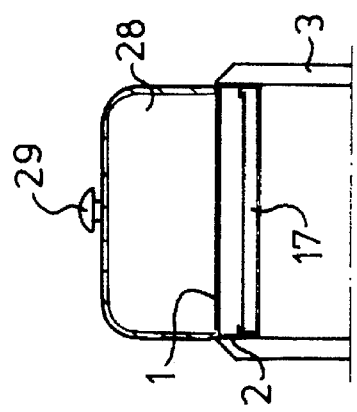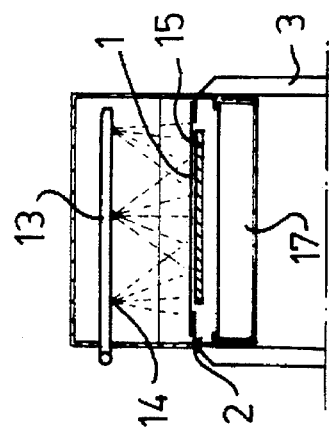

METHOD, COMPOSITION AND DEVICE FOR THE TREATMENT OF RAW MATERIALS, PRODUCTS AND PRODUCTION MEANS, IN PARTICULAR IN THE FOODSTUFFS INDUSTRY

FIELD OF THE INVENTION

The invention relates to a method for the treatment of raw materials, products and production means, in particular of water and of materials and equipment in the foodstuffs industry, in which use is made of hydrogen peroxide.

The invention also relates to an agent which can be used in this method.

BACKGROUND OF THE INVENTION

The contamination of raw materials and processed products with harmful biological material is regarded as a drawback to public health and the environment to an ever increasing extent. Increasingly stringent demands with regard to the bacteriological state are being made, in particular in respect of materials and equipment which are used in the foodstuffs industry. The problem is particularly acute in the case of, for example, processes in the foodstuffs industry in which conveyor belts and the like are used and the process is carried out at room temperature, because under such conditions it is difficult to control and combat pathogens and other harmful constituents.

It is known to improve the shelf life of foodstuffs by adding chemicals. According to U.S. Pat. No. 2053740, hydrogen peroxide can be added to milk and cream, or substances which generate hydrogen peroxide under the action of enzymes can be added to foodstuffs (German Patent 2420135). Monohydric and polyhydric alcohols can also be used for the treatment of foodstuffs (EP-A-169927, DE-A-2119351, GB-A-1273938 and GB-A-1375704). The addition of sulphite in order to keep the contamination of foodstuffs to an acceptable level is also generally known. Chlorine is frequently used for cleaning and disinfecting production equipment. Moreover, the use of chemicals entails the risk that the dosage may be too high, as a result of which carcinogenic or allergic effects can sometimes arise. The use of chlorine can also lead to corrosion of metal-containing apparatus, which in turn can form a source of contamination with bacteria. A further disadvantage of the chemical agents used to date is that the excess of the agents is entrained with cleaning water and therefore can pollute the environment.

A solution to problems of this type has been sought in working in a sterile room or in the use of effluent treatment. Water-treatment devices of this type are usually designed on the basis of the average water quality, the bacteriological pollution and the effluent standards. Disruptions in production frequently lead to overloading of the device, as a result of which it is again necessary to resort to chemicals in order to meet the production requirements. These various factors lead to a sometimes unacceptable increase in costs and environmental pollution.

There is therefore great need for an inexpensive and simple method for the treatment of raw materials, products and production means, and also of process water from such a production. A method, a composition and a device have been found with which it is possible to meet this need.

SUMMARY OF THE INVENTION

The method according to the invention as described in the preamble is, to this end, characterized in that the raw materials, products and/or production means are treated with a mixture of hydrogen peroxide and glycerol.

In particular, the materials are treated with a solution of hydrogen peroxide and glycerol in a ratio of between 1:1 and 10:1, more particularly between 2:1 and 5:1, in water.

Preferably, a solution is used which, in addition to hydrogen peroxide and glycerol, also contains an organic acid as stabilizer, such as acetic acid, lactic acid, benzoic acid or hexanoic acid, and in particular valeric acid (pentanoic acid). This organic acid is preferably present in an amount of 1–5% by weight with respect to the hydrogen peroxide.

Preferably, the means or materials are treated by atomizing the above-mentioned solution in the room in which the means or materials are located. This method of treatment is very efficient, with a very low consumption of preservative, because the treatment takes place in the gas phase. The composition according to the invention gives rise both to a disinfectant action and to a long-term preservative action. The foodstuffs treated are not adversely affected by the additives.

When treating foodstuffs, preferably an amount of the solution is used such that 0.1–1 g of hydrogen peroxide is applied per kg of foodstuffs.

The treatment according to the invention is carried out in particular at a temperature of between 5° and 70° C. for about 1 minute to about ½ an hour, depending on the treatment temperature and the concentration of the solution in the room.

In order further to increase the shelf life of the products, such as, for example, foodstuffs, treated with the mixture according to the invention, a further embodiment of the invention provides for surface-drying of treated products by means of sterile air, optionally heated to above room temperature. This is because the removal of water from the treated products is an important precondition for prevention of bacterial division. Indeed, an anhydrous surface forms a poor environment for the bacteria.

As a result of the coating which the composition according to the invention forms on the treated product, the liquid content (water content) of the product is not affected, or is barely affected, by drying. In order to improve the adhesion of the composition to the product, in yet a further embodiment of the method according to the invention the treated product is subjected to the drying step only after a certain time.

The composition according to the invention is characterized in that it consists of a solution of hydrogen peroxide and glycerol in water, preferably demineralized water. The weight ratio of hydrogen peroxide to glycerol is preferably between 1:1 and 10:1 and more preferentially between 2:1 and 5:1. The solution preferably contains 10–50% by weight, in particular 25–35% by weight, of hydrogen peroxide.

Preferably, the solution also contains a stabilizer in the form of an organic acid. The organic acid is in particular valeric acid in an amount of 1–5% by weight with respect to the hydrogen peroxide.

According to the invention, use is made of hydrogen peroxide as the basis for the treatment composition. The use of this agent is already known per se, but it has been little used to date in the foodstuffs industry and where it has been used this has been as an additive to the foodstuffs. One problem with hydrogen peroxide is that it decomposes rapidly, so that the addition thereof has little effect, unless high concentrations are used. An example of such use of hydrogen peroxide is described in U.S. Pat. No. 2053740 which has already been mentioned, and German Patent 2420135 which has also already been mentioned.

The surprising feature of the present invention is that when hydrogen peroxide is mixed with glycerol, and optionally a stabilizing organic acid, in a solution in water and this solution is atomized on or around the untreated or treated foodstuffs or devices an effective disinfection and/or preservation takes place, essentially all bacteria and pathogens and the like being eliminated after a short time has elapsed. The products treated in this way are also protected for a considerable time against fresh contamination. The solvent used is preferably demineralized water; demineralized water is understood to be water from which minerals and organic substances have been removed.

The preserving effect also occurs when materials or articles are exposed directly to an aqueous solution. Thus, for example, parts of production means, which cannot be subjected to an atomization treatment, can be treated with the mixture and, furthermore, process grater and domestic waste water can also be treated by adding the mixture in liquid, optionally further concentrated, form. Treatment with the composition according to the invention can therefore be carried out in diverse ways, for example by spraying, irrigation, immersion, rinsing and the like. Atomization can also be carried out in accordance with the principle of an air humidifier and be used for the storage of foodstuffs, for example in refrigerated or deep-freeze chambers for the storage of foodstuffs such as potatoes, or without special cooling provisions.

The disinfecting effect of hydrogen peroxide is based on the splitting of hydrogen peroxide into water and oxygen. Normally, this splitting already proceeds rapidly at room temperature and proceeds even more rapidly at elevated temperature and, furthermore, evaporation of hydrogen peroxide also takes place, so that the residence time of hydrogen peroxide is too short to effect removal of contamination from large quantities of foodstuffs. Surprisingly, the addition of glycerol is found to retard the splitting of hydrogen peroxide in such a way that the effect of the composition is greatly improved. The glycerol which is used for this purpose must be as pure as possible and is preferably of a grade which is permitted for use in the foodstuffs industry.

A further improvement in the intended effect is found to be achieved by adding an organic acid. This organic acid can be a carboxylic acid, such as benzoic acid, acetic acid, propionic acid and higher fatty acids, or a mono- or di-hydroxycarboxylic acid, such as lactic acid. A carboxylic acid which is found to give a particularly good improvement in the effect is valeric acid. The latter also is preferably used in a grade which is permitted in the foodstuffs sector. If the mixture of hydrogen peroxide, glycerol and, optionally, valeric acid is sprayed in the room around the materials to be treated, this is preferably carried out in such a way that the hydrogen peroxide concentration in the air is 0.001 to 0.01% by volume. The treatment time is dependent on the concentration of the mixture in the atmosphere and on the temperature. At a concentration of between 0.001 and 0.005% by volume and a temperature of 5° to 25° C., the treatment time will usually be between 2 and 5 minutes. In the case of treatment with the mixture in the form of a solution having a concentration of 0.2–0.3% by weight of hydrogen peroxide and at a temperature of 50° to 60° C., the treatment time will usually be between 5 and 30 minutes.

The mixture of hydrogen peroxide, glycerol and, optionally, organic acid according to the invention is a clear and virtually odourless fluid which has a slight acid reaction. The mixture has a broad action and, inter alia, renders harmless Gram-positive bacteria, moulds and algae, counteracts slime formation and produces no foaming. Treatment of foodstuffs with the mixture generates no odour, discolouration or taste. The mixture can be used in the entire foodstuffs industry, in the production, the treatment and the storage of foodstuffs.

The invention also relates to a device for carrying out the method described above in a simple and inexpensive manner. The device can be used in either large or small production units. The device according to the invention comprises conveyor means for the material or product to be treated and at least one treatment chamber through which the material or product can be passed and is characterized in that the treatment chamber is provided with means for atomization and/or spraying of a liquid composition and with means for metering, pumping and removing the composition.

With a view to efficient use of the composition according to the invention, a further embodiment of the device according to the invention is characterized in that said device comprises two or more connected treatment chambers or areas, means also being provided with which liquid which leaves one chamber can be introduced into another chamber.

In yet a further embodiment of the device according to the invention, the conveyor means are a conveyor belt in gauze form, the treatment chamber having openings at both ends for the conveyor belt, and the chamber being provided with a container for treatment liquid, a metering pump, a booster and an air/liquid mixer which is connected to a line for the supply of a mixture of liquid and air to the treatment chamber, and is also provided with an internal piping system consisting of one or more lines which are connected to spray tubes which are provided with openings for administering atomized liquid into the treatment chamber, which is also provided with a discharge.

In order to bring the product into optimum contact with the treatment liquid, a vibrator or vibrating frame is also provided, with which the product is gently shaken in the treatment chamber in such a way that no damage or settling occurs and the product does not jump from the conveyor means.

In the preferred embodiment of the device according to the invention, a drying chamber installed downstream of the treatment chamber is also provided for drying the surface of the treated product with sterile air. Here also, a vibrator or vibrating frame can again be used for gently shaking the product. This is provided in order to ensure optimum drying.

In order to ensure good adhesion of the additive to the product, in yet a further embodiment of the device according to the invention a rest chamber is installed between the treatment chamber and the drying chamber. The conveyor belt can advantageously extend as a single belt through these chambers.

With regard to the device according to the invention, it can be stated that the device can be of relatively simple design, consisting of a treatment chamber, in which means are located for the supply of the mixture and for the mixing thereof with air, the temperature, which preferably can be controlled, and the dimensions of the chamber being adapted to the desired application. Treatment can be effected by passing the materials at a suitable, adjustable speed through the treatment chamber. By adding a drying chamber and, if desired, a rest chamber, a further increase in, for example, the shelf life of a treated foodstuff can be achieved.

The invention is suitable in particular for the preserving treatment of readily perishable goods, such as fish and other seafood. Meat products can also be treated using the method according to the invention, without the quality, colour, nutritional value or taste thereof being affected. The shelf life can be significantly extended by this means. Process water from the foodstuffs industry can also be treated using the method according to the invention and in this way level of purification which meets environmental requirements can be achieved.

BRIEF DESCRIPTION OF THE DRAWINGS

FIG. 1 shows schematically a side view of a preferred embodiment of a device which is suitable for carrying out the method according to the invention.

FIGS. 2, 3 and 4 show, schematically, cross-sectional views of the device according to FIG. 1.

DETAILED DESCRIPTION OF THE INVENTION

Figure 5:
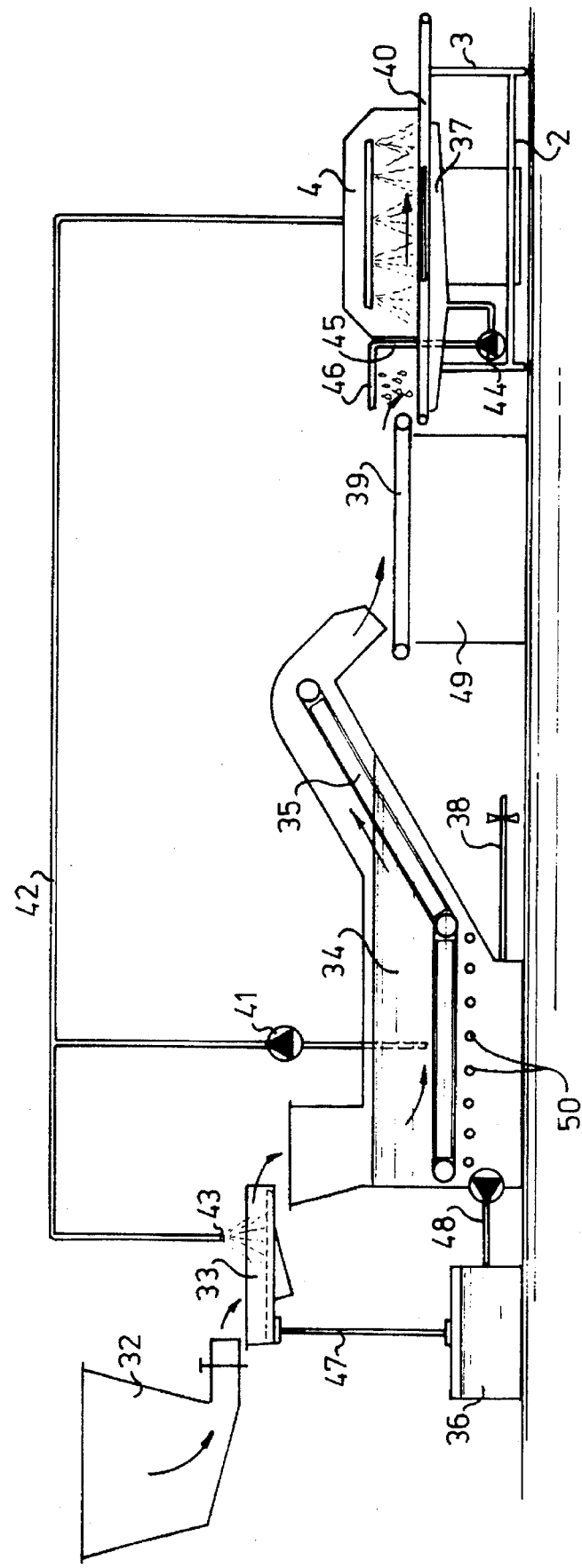
FIG. 5 shows schematically a set-up for one use of the method according to the invention.

The device according to FIG. 1 consists of a stainless steel or plastic conveyor belt 1 which is in the form of a gauze and has a controllable electrical drive motor 6, which is placed in a frame or stand 2 with adjustable legs 3. Conveyor belt 1 passes through a stainless steel treatment chamber 4 which has a discharge 5. A liquid container 7 for the disinfection composition is located outside the chamber 4 itself, but is integrally connected thereto. The container is connected via lines 8 to a high-pressure pump 9 and an air/liquid mixer 10 with booster 11 and is also connected to a number of tubes 12 which run parallel to the conveyor belt and distribute the mixture over the treatment chamber 4 and a number of transverse tubes 13 which are connected to the parallel tubes 12 and are provided with spray openings 14 and which ensure uniform atomization of liquid through the chamber 4. This set-up ensures that material which is located on the conveyor belt 1 is exposed to the agent from all sides. All components of the device are electrically driven. The tube system can be made of stainless steel or, for example, high-grade plastic, depending on the product to be treated.

In order to ensure that the products to be treated are brought into contact in their entirety with the treatment liquid, in the preferred embodiment of the device according to the invention the belt 1 runs over a vibrating frame 15. This vibrating frame 15 is preferably vibrated by means of an electromagnetic vibrator 16. The vibration is adjusted such that the product is shaken gently without it being damaged, that is to say without the product jumping up or settling on the belt.

The mixture of hydrogen peroxide, glycerol and, optionally, valeric acid in demineralized water is fed to the mixer 10 by means of the pump 9. At the same time, booster 11 blows air into the mixer 10 under excess pressure. The treatment mixture is then atomized via the spray system 14 on the inside of the treatment chamber 4 over the material on the conveyor belt 1.

The air to be used is sucked in via an air-clean air filter. Intimate mixing of the sterile air and the liquid agent takes place in the mixer 10, the agent being injected axially into the stream of air. The composition of the air/liquid mixture can be adjusted, for example by varying the pump opening.

The movement of the conveyor belt 1 coupled with the atomization of the air/liquid mixture in the treatment chamber 4 gives optimum contact between the materials and the treatment mixture according to the invention. The conveyor speed of the belt 1 depends, inter alia, on the product to be treated, the bacteriological nature thereof and the desired degree of preservation. An excess pressure in the treatment chamber 4 prevents the ingress of contaminating air into the chamber. Liquid mixture which leaks from the treatment chamber into the production line area will have an additional disinfectant action here and thus ensure a cleaner production.

The liquids which drip from the product to be treated are collected in a drip pan 17 located below the conveyor belt 1. This measure is provided in order to prevent potential contamination of the floor 18 under the frame 2. The relevant liquids pass to a condensate filter reservoir 19. In this reservoir 19 any solid particles (originating from the product to be treated) are separated off from the liquids by means of a sieve plate 20. The residual liquids then pass via the discharge 5 to a collection container 21.

If an optional packaging device is set up immediately downstream of the treatment chamber 4, the packaged products will be able to contain hardly any or no contaminating germs.

In the preferred embodiment, the device according to the invention also comprises a drying chamber 22, in which the product treated in the chamber 4 is freed, by means of sterile air, from the residual liquid which still adheres to the outside of the product. A vibrating frame 23, over which the conveyor belt 1 runs and which is driven via an electromagnetic vibrator 24, is also located in the drying chamber 22. The vibrating frame 23 ensures that, by gently shaking the product, the drying air comes into optimum contact with the surface of the product. The drying air is sucked in from the production area by means of a booster 25 via an air-clean filter 26. Sterile air is then introduced into the drying chamber 22 via a tube system 27. The amount and, if desired, the temperature of the air are matched to the product to be dried, i.e. the amount of adhering liquid, by means of adjustment of the booster 25 and heating means (not shown).

In order to improve the adhesion of treatment liquid to the product, a rest chamber 28 is preferably located between the treatment chamber 4 and the drying chamber 22. In the preferred embodiment of the device according to the invention, the rest chamber 28 is in the form of a tunnel, through which the conveyor belt 1 runs. In this tunnel the treatment liquid further adheres to the product. With this arrangement, the drip pan 17 mounted below the conveyor belt 1 extends from below the treatment chamber 4 past the rest chamber 28 to the drying chamber 22.

In order to remove oxygen molecules liberated during decomposition, vents 29 are mounted on the rest chamber 28. These relieve pressure but prevent ingress of contaminated air from the outside. The drying air which has been in contact with the product in the drying chamber 22 will, as a result of its excess pressure, leave the drying chamber via a vent 30 mounted on the top thereof. This vent 30, like the vents 29 of the rest chamber 28, will also be provided with a pressure relief safety feature or non-return valve, which can be adjusted to a specific pressure so as to ensure a minimum excess pressure in the rest chamber and drying chamber.

The housing of the drying chamber 22 and the rest chamber 28 is preferably made of stainless steel or high-grade plastic. The rest chamber 28 can also be made of transparent plastic, for visual monitoring. The tube system 27 of the drying chamber 22 is preferably made of plastic tubing, for reasons of costs. The outlets 31 of the tubes 27 are arranged in such a way that all sides of the product come directly into contact with the drying air. When the product leaves the drying chamber 22 it is ready for vacuum-, gas- or other packaging or storage. As a supplement to the liquid treatment, the shelf life of, for example, a foodstuff has been substantially increased by the supplementary drying process, without any appreciable adverse effect on the taste, nutritional value, colour, weight, etc. of the product.

FIG. 2 shows a partial cross-section through the treatment chamber 4, taken along the line II—II in FIG. 1. FIG. 3 shows a partial cross-section through the rest chamber 28, taken along the line III—III in FIG. 1. FIG. 4 shows a cross-section along the line IV—IV of the drying chamber 22 shown in FIG. 1. The arc-shaped arrangement of the air outlets 31 in the drying chamber 22, in order to effect contact of drying air and product on all sides, can clearly be seen.

In a practical embodiment of the device according to the invention, the air/liquid mixer 10 is so constructed that the air which leaves the mixer 10 does not release the entrained liquid on leaving the mixer, which to this end is of parabolic shape with a screw on the inside. The storage container 7 is made of stainless steel; the collection container 21 is made of plastic and the frame is also made of stainless steel, such as RVS 312 or 304. The air filters in the booster 11 and the drying chamber are designed as air-clean filters, consisting of a flint filter, electrostatic filter, an active carbon filter and an ionizer.

A set-up of this type, which consists of a treatment chamber 4 and, optionally, a rest chamber 28 and drying chamber 22 with accessories as explained above can be adapted to various sizes and types of production lines, can be of mobile design, has relatively low purchase cost and is simple to operate and thus rapidly cost-saving.

In the production line which is shown in FIG. 5, mussels for consumption are prepared. The production line consists of a boiling apparatus or autoclave 32, a vibrating or shaking apparatus 33 for removing the shell from the mussel, a rinsing bath 34 with conveyor belt 35, a picking or sorting belt 39 with waste bin 49 and a conveyor belt which fits in a treatment chamber 4 with atomization facilities as described in FIG. 1. The various units are mutually arranged as shown. The products, i.e. the mussels, move in the direction of the arrow. The shaking apparatus 33 and the rinsing bath 34 are connected via lines and 48, respectively, to a reservoir 36 for the collection of waste products. The chamber 4 is connected to a collection reservoir 57. The treatment agent collected is re-used at other locations in the production line, for example the shaking apparatus 33, with the aid of a tube system and pumps.

Fresh mixture according to the invention, in a suitable concentration mixed with demineralized water, is supplied via an inlet 38 to the rinsing bath 34 for rinsing the product from which the shell has been removed. The spray mixture is mixed with clean air in the rinsing bath via air inlets 50 and is fed via a pump 41 and a line system 42 to a sprayer 43, which is located above the shaking apparatus 33, and additionally is atomized under pressure in the treatment chamber 4. The liquid from the treatment chamber 4 is collected in the reservoir 37, from where one fraction can be fed via a pump 44 through a line system 45 to a drip device 46 which is located downstream of the sorting belt 39 and another fraction can be re-atomized under pressure in the treatment chamber 4. If desired, several treatment chambers 4 can be used downstream of one another, it also being possible to arrange a rest chamber 28 and drying chamber 22 according to FIG. 1 downstream of the conveyor belt 40.

The advantage of rinsing the product with fresh treatment liquid is that the total amount of liquid is substantially reduced and already used liquid is utilized for partial disinfection of the product in an early stage of the production line, that is to say at the shaking apparatus 33 and downstream of the sorting belt 39. In this way about 80% of the bacteria and pathogens can already be removed prior to the treatment in the chamber 4 and the remaining approximately 20% can be rendered harmless as a consequence of treatment in the chamber 4 and by means of optional post-rinsing with (fresh) treatment liquid (not shown). In the reservoir 36 live bacteria may remove proteins from the waste water, such that the waste water becomes foam-free. This disinfection process gives an effluent which does not pollute the environment.

The result of checks on the mussel production line subjected to the treatment described indicated a number of contaminating germs of 60–100 germs/g of product, Enterococcus sp. of less than 10 bacteria/g of product and Staphylococcus sp. of less than 50 bacteria/g of product.

In the poultry sector, the invention is outstandingly suitable for rendering table and hatching eggs salmonella-free.

I claim:

1. Composition for the treatment of at least one of raw materials, products and water, consisting essentially of 10–50% by weight of hydrogen peroxide, and glycerol, wherein the weight ratio of hydrogen peroxide to glycerol is 1:1 to 10:1.

2. Composition according to claim 1, wherein the composition contains a solution of hydrogen peroxide and glycerol in a weight ratio of 2:1 to 5:1 in water.

3. Composition according to claim 1, wherein the composition contains 25–35% by weight of hydrogen peroxide.

4. Composition for the treatment of at least one of raw materials, products and water, consisting essentially of an organic acid, glycerol and 10–50% by weight of hydrogen peroxide, wherein the weight ratio of hydrogen peroxide to glycerol is 1:1 to 10:1.

5. Composition according to claim 4, wherein the organic acid is valeric acid.

6. Composition according to claim 4, wherein the composition contains 1–5% by weight of organic acid with respect to the hydrogen peroxide.

7. Method for the treatment of at least one of raw materials, products and water, which comprises treating said at least one of raw materials, products and water with a composition consisting essentially of 10–50% by weight of hydrogen peroxide, and glycerol, wherein the weight ratio of hydrogen peroxide to glycerol is 1:1 to 10:1.

8. Method according to claim 7, wherein the composition is atomized in the room surrounding said at least one of raw materials, products and water.

9. Method according to claim 8, wherein a hydrogen peroxide concentration in air of 0.001 to 0.01% by volume is introduced in the room.

10. Method according to claim 7, wherein the treatment is carried out at a temperature of 5°–70° C. for 1 to 30 minutes.

11. Method according to claim 7, wherein an amount of the composition corresponding to 0.1–1 g of hydrogen peroxide per kg of raw material, product or water is used for the treatment.

12. Method according to claim 7, further comprising drying the treated raw material, product or water at the surface using sterile air.

13. Method according to claim 7, wherein the raw material, product or water treated is foodstuff.

14. Method for the treatment of a foodstuff, which comprises treating said foodstuff with an effective amount of a composition consisting essentially of an organic acid, glycerol and 10–50% by weight of hydrogen peroxide, wherein the weight ratio of hydrogen peroxide to glycerol is 1:1 to 10:1.

* * * * *